(12) United States Patent
Sogaro

(10) Patent No.: US 9,004,796 B2
(45) Date of Patent: Apr. 14, 2015

(54) APPLICATION DEVICE

(75) Inventor: Alberto C. Sogaro, Kronberg (DE)

(73) Assignee: Sulzer Mixpac AG, Haag (CH)

( * ) Notice: Subject to any disclaimer, the term of this patent is extended or adjusted under 35 U.S.C. 154(b) by 1454 days.

(21) Appl. No.: 12/673,108

(22) PCT Filed: Aug. 4, 2008

(86) PCT No.: PCT/DE2008/001287
§ 371 (c)(1),
(2), (4) Date: Oct. 12, 2011

(87) PCT Pub. No.: WO2009/024117
PCT Pub. Date: Feb. 26, 2009

(65) Prior Publication Data
US 2012/0034012 A1    Feb. 9, 2012

(30) Foreign Application Priority Data
Aug. 20, 2007 (DE) .......................... 10 2007 039 177
Jan. 31, 2008 (DE) ...................... 20 2008 001 427 U

(51) Int. Cl.
*A45D 34/04* (2006.01)
*A61M 35/00* (2006.01)
*A46B 9/00* (2006.01)
*A61C 5/06* (2006.01)
(Continued)

(52) U.S. Cl.
CPC ............. *A61M 35/003* (2013.01); *A45D 34/04* (2013.01); *A45D 2200/055* (2013.01); *A45D 2200/1018* (2013.01); *A46B 9/005* (2013.01); *A46B 11/0024* (2013.01); *A46B 11/0079* (2013.01); *A46B 2200/1046* (2013.01); *A46B 2200/20* (2013.01); *A61C 5/06* (2013.01); *A61M 2005/3106* (2013.01)

(58) Field of Classification Search
USPC ......... 401/132–134, 151, 170, 196, 202, 261, 401/269, 272
See application file for complete search history.

(56) References Cited

U.S. PATENT DOCUMENTS

| 186,723 | A | * | 1/1877 | Goehring ...................... 401/170 |
| 4,068,974 | A | * | 1/1978 | Meyer et al. .................. 401/150 |

(Continued)

FOREIGN PATENT DOCUMENTS

| DE | 40 16 353 A1 | 12/1990 |
| DE | 199 56 705 C2 | 11/1999 |

(Continued)

OTHER PUBLICATIONS

International Search Report corresponding to PCT/DE2008/001287 under date of mailing of Jul. 20, 2009.

*Primary Examiner* — David Walczak
*Assistant Examiner* — Bradley Oliver
(74) *Attorney, Agent, or Firm* — Quarles & Brady LLP

(57) ABSTRACT

An application device for applying a flowable substance includes an outer shell, and inner shell, and a reservoir defined between the inner and outer shells. The outer shell has an outer circumferential wall and an outer bottom. The inner shell has an inner circumferential wall and an inner bottom defining an inner space and is sealingly received in the outer shell for telescopic movement between a closed position and a released position. At least one orifice is formed in the inner bottom of the inner shell. A closure means closes off the at least one orifice in the closed position, wherein at least one pin forming at least part of the closure means extends from the outer shell.

13 Claims, 3 Drawing Sheets

(51) Int. Cl.
  *A46B 11/00*    (2006.01)
  *A61M 5/31*    (2006.01)

(56)      References Cited

U.S. PATENT DOCUMENTS

| 4,747,719 | A | 5/1988 | Parkin | |
| D319,662 | S * | 9/1991 | Henry | D19/43 |
| 5,609,581 | A * | 3/1997 | Fletcher et al. | 604/212 |
| 6,719,729 | B2 * | 4/2004 | Sogaro | 604/191 |
| 6,776,549 | B2 * | 8/2004 | Gueret | 401/170 |
| 6,786,667 | B1 * | 9/2004 | Thomas et al. | 401/134 |
| 7,131,784 | B2 * | 11/2006 | Lee et al. | 401/128 |
| 7,153,053 | B1 | 12/2006 | Wiley | |
| 8,348,913 | B2 * | 1/2013 | Hoang et al. | 604/310 |
| 8,550,737 | B2 * | 10/2013 | Ruiz et al. | 401/134 |
| 2002/0044816 | A1 * | 4/2002 | Strauss | 401/123 |
| 2002/0087122 | A1 * | 7/2002 | Sogaro | 604/191 |
| 2003/0063945 | A1 * | 4/2003 | Gueret | 401/170 |
| 2008/0245314 | A1 * | 10/2008 | Brodowski et al. | 119/651 |
| 2013/0108352 | A1 * | 5/2013 | Ruiz et al. | 401/132 |

FOREIGN PATENT DOCUMENTS

| DE | 601 13 035 T2 | 6/2006 |
| EP | 0 627 229 A1 | 6/1993 |
| EP | 1 293 448 A | 7/2002 |
| EP | 1 743 700 A1 | 1/2007 |
| WO | 01 32242 A1 | 5/2001 |

\* cited by examiner

APPLICATION DEVICE

CROSS-REFERENCE TO RELATED APPLICATIONS

This application claims priority to PCT International Application No. PCT/DE08/001287 filed on Aug. 4, 2008, which claims priority to German Application No. 10 2007 039 177.5 filed on Aug. 20, 2007, and German Application No. 20 2008 001 427.1 filed on Jan. 31, 2008, both of which are fully incorporated by referenced herein.

The invention relates to an applicator device for applying a flowable substance.

Known for example from EP 1 743 700 A1 is an applicator device in the form of a pipetting device formed from an outer shell and an inner shell. The inner shell is configured pot-shaped and comprises a closed bottom as well as a circumferential wall provided with several orifices. In addition, the inner shell is guided gas-tight internally at the circumferential wall of the outer shell and can be telescoped between a closed position and a released position. In the closed position the inner shell reservoirs a flowable substance. Telescoping the inner shell into the released position enables the substance reservoired in the inner shell to flow through the orifices in the circumferential wall into the outer shell from where it is applied.

The invention is based on the object of providing an applicator device configured compact and simple to activate.

This object is achieved in accordance with the invention by the applicator device having the features as set forth in claim 1.

Consequently, in accordance with the invention an applicator device for applying a flowable substance is proposed, comprising an outer shell which has an outer circumferential wall and an outer bottom, an inner shell which has an inner circumferential wall and an inner bottom and which is guided gas-tight in the outer shell and which is telescopable between a closed position and a released position, whereby the inner bottom of the inner shell comprises at least one orifice, which in the closed position of the inner shell is closed off by a closure means and in the released position of the inner shell allows the flowable substance to pass through at least partially, whereby in telescoping the inner shell from the closed position into the released position an inner space of the inner shell is charged by displacement of the flowable substance received in the reservoir between the outer shell and the inner shell.

The gist of the invention is consequently to provide an applicator device in which the inner shell acts as a plunger so that telescoping inner shell and outer shell together enables the substance held in the reservoir to flow through the orifice in the bottom of the inner shell into the interior of the inner shell. In the closed position, i.e. when inner shell and outer shell are telescoped away from each other, the orifice in the bottom of the inner shell is closed off so that no liquid can flow from the reservoir into the interior of the inner shell. When the device is activated the orifice is released open.

In one preferred embodiment of the device in accordance with the invention an applicator element is provided which engages the inner shell at least partly. Telescoping the inner shell from the closed position into the released position wets the applicator element with the flowable substance held in a reservoir between the outer shell and the inner shell in the closed position.

In another preferred embodiment of the device in accordance with the invention a pin oriented axially relative to the outer shell is configured at the bottom of the outer shell. This pin or spike preferably serves to seal the orifice in the bottom of the inner shell in the closed position of the inner shell. In this case the pin thus forms the means for closing off the orifice. Activating the applicator device urges the pin through the orifice in the bottom of the inner shell enabling the substance held in the reservoir to flow into the interior of the inner shell.

To effectively seal and also to release the orifice in the bottom of the inner shell the pin comprises at its end proximal to the outer bottom of the outer shell a widened portion, the cross-sectional area of which substantially corresponds to the cross-sectional area of the orifice. In the closed position of the inner shell the widened portion closes off the orifice. The widened portion or portion having an enlarged diameter may, of course, also be a middle portion of the pin. In this case the pin fully extends through the orifice in the closed position.

In the closed position the pin may feature a sealing lip or other sealing means in the portion level with the orifice, i.e. in the widened portion. The sealing lip whose configuration itself may result in the widened portion or portion having an enlarged diameter and which may be seated in an annular groove of the pin, can cooperate with an annular groove at the bottom of the inner shell arranged in the region of the circumference of the orifice of the inner shell and engaging the sealing lip in the closed position of the inner shell. As an alternative, a sealing lip also configured at the bottom of the inner shell may in the closed position contact the widened portion, i.e. portion having an enlarged diameter where a corresponding annular groove is configured which is engaged by the sealing lip in the closed position.

In another alternative embodiment the closure means is formed by a portion of the bottom of the inner shell configured as a frangible knockout. Telescoping the inner shell from the closed position into the released position causes the frangible knockout to be pierced by the pin to release the orifice at least partly so that the flowable substance can flow from the reservoir into the interior of the inner shell when the device in accordance with the invention is activated.

Preferably the frangible knockout is formed by a material weakening or diminution of the inner shell in the corresponding portion of the bottom of the inner shell.

To facilitate activating the applicator device in accordance with the invention the inner shell is provided with a finger-grip in one preferred embodiment.

The finger-grip is configured, for example, as a shroud clasping the outer surface of the circumferential wall of the outer shell at least in the released position at least partly. The shroud may in addition comprise at its outer wall a collar configured concave relative to the device as a finger-grip, so that, for example, the inner shell can then be held between index finger and middle finger and thumbing the bottom of the outer shell activates the applicator device.

To prevent the flowable substance from being inadvertently delivered by the device in accordance with the invention in the closed position a sealing means is disposed to advantage between the inner shell and the outer shell. The sealing means comprises, for example, a sealing lip cooperating with at least one annular groove. The sealing lip is arranged, for example, at the inner wall of the outer shell and the annular groove at the outer wall of the inner shell.

To provide the user with a tactile indication of the closed position and/or released position the device in accordance with the invention may comprise a detent means defining the closed position and/or the released position. This detent means may be formed by the sealing lip/annular groove combination as described above.

The applicator device in accordance with the invention is particularly suitable for applying medications and/or cosmetic products. For example, the reservoir may hold a medication for treatment of a skin malady, for example a liquid for treating acne, although it is just as possible that the flowable substance is a substance as used in dental practice, for example, a bleaching paste or gel.

The applicator element may be configured particularly as a sponge, brush or the like, although it is just as possible that the applicator element is configured as a pipette in which case the applicator element may be engineered in one piece with the inner shell of the applicator device in accordance with the invention.

When the applicator element is configured as a sponge or brush it is particularly an advantage when the applicator element is fully received by the inner shell in the closed position of the inner shell and protrudes at least partly in the released position. This design prevents the applicator element from becoming tainted or damaged in the closed position of the applicator device in accordance with the invention, i.e. when being transported.

To shift the applicator element relative to the inner shell in enabling it to be urged from the inner shell when the device in accordance with the invention is activated the applicator element comprises to advantage a bottom surface which can be engaged by the pin or spike. However, it is also possible that the applicator element is directly connected to the pin configured at the outer bottom of the outer shell to cooperate with the orifice in the inner bottom of the inner shell.

To prevent inner shell and outer shell from being accidentally telescoped together in the closed position of the device, a safeguarding means may be provided formed, for example, as a tear tab clasping the inner shell between an annular collar of the outer shell and an annular collar or shroud of the inner shell in the closed position.

Furthermore, the inner shell may feature a cap which in the closed position of the device in accordance with the invention covers and protects the applicator element arranged in the inner shell. Preferably the cap is configured integrally with the inner shell and hinged thereto by a film hinge or the like. Preferably the cap is configured as bistable element which is biased up to a certain opening angle in the closing direction and as of a certain opening angle in the opening direction, so that the cap automatically snaps into place when the opening angle is attained.

Further advantages and advantageous aspects of the subject matter of the invention are disclosed in the description, drawing and in the claims.

Two example embodiments of the applicator device in accordance with the invention will now be detailed as depicted diagrammatically simplified in the drawing in which.

Figure 1:
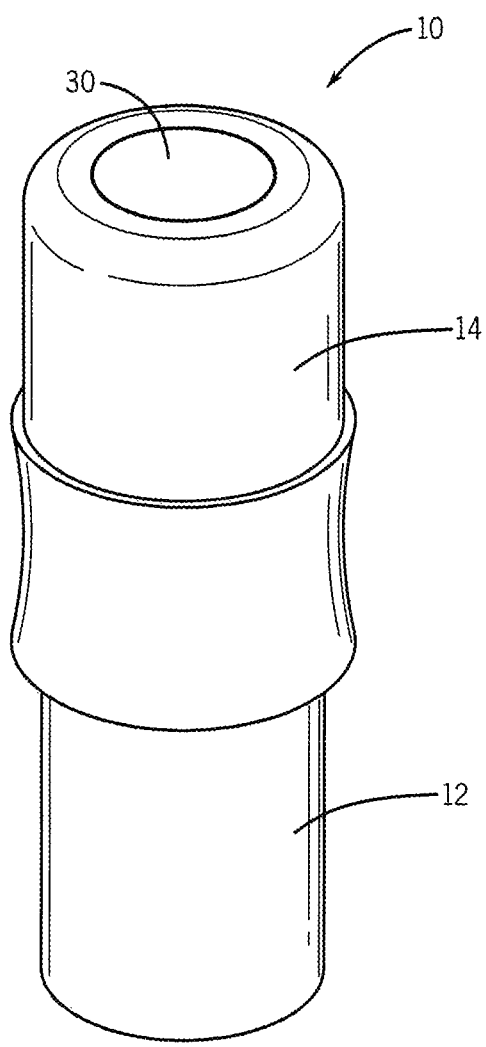
FIG. 1 is a view in perspective of an applicator device for applying a liquid.
Figure 2:
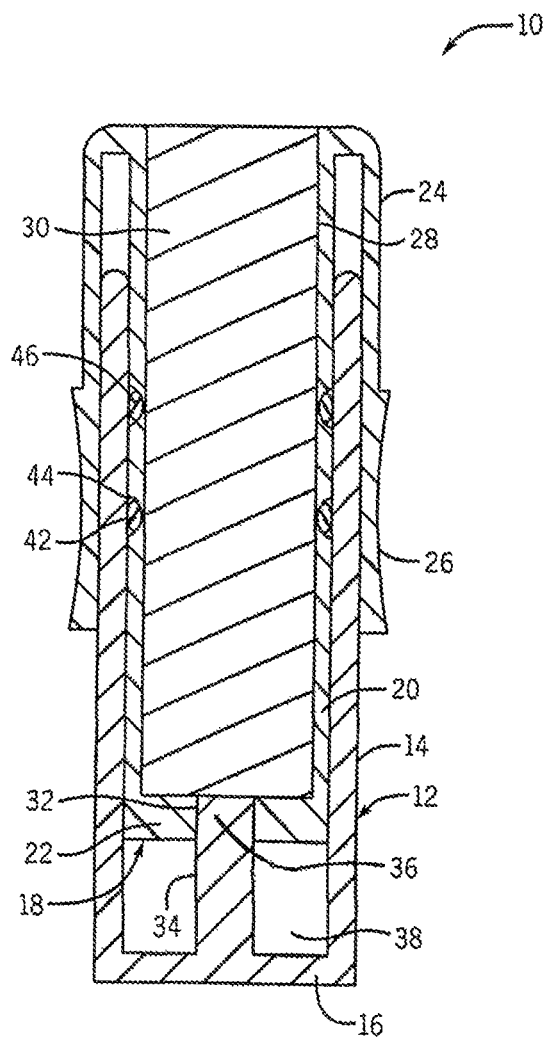
FIG. 2 is a longitudinal section through the applicator device as shown in FIG. 1.

Referring now to FIGS. 1 and 2 there is illustrated an applicator device 10 configured pencil-shaped and serving to apply a liquid substance, such as an acne medication, to the skin of a patient.

The applicator device comprises a substantially pot-shaped plastics outer shell 12 featuring an outer circumferential wall 14 and an outer bottom 16. At its end proximal to the outer bottom 16 the cylindrical outer shell 12 is configured open.

The applicator device 10 comprises furthermore a likewise substantially pot-shaped plastics inner shell 18 inserted into the open end of the outer shell 12 in which it is slidingly guided.

The inner shell 18 comprises an inner circumferential wall 20 and an inner bottom 22 of the applicator device 10.

Configured at the inner shell 18 is a shroud 24 molded to the inner shell 18 at the end proximal to the bottom 22 and partly shrouding the circumferential wall 14 of the outer shell 12. The shroud 24 and the inner circumferential wall 20 of the inner shell 18 form an annular space for receiving an end portion of the circumferential wall 14 of the outer shell 12. Provided at the shroud 24 is an annular collar 26 formed concave relative to the outer shell 12 and serving as a finger-grip.

In addition, an interior 28 of the inner shell 18 surrounded by the circumferential wall 20 is filled out by an applicator element 30 configured as a sponge, by means of which the corresponding liquid can be applied to the skin.

The inner bottom 22 of the applicator device 10 comprises a circular orifice 32 cooperating with a pin 34 protruding from the outer bottom 16 of the outer shell 12 such that a thickened end portion 36 of the pin 34 closes off the orifice 32 in a closed position as shown in FIG. 2. In a released position in which the inner shell 18 is telescoped further into the outer shell 12 than in the closed position, the pin 34 fully extends through the orifice 32 so that between the bottom 22 and the pin 34 an annular surface area is released via which a flowable substance can flow.

In the closed position as shown in FIG. 2 the flowable substance or acne medication is received in a reservoir 38 defined by the inner bottom 22, outer bottom 16 and outer circumferential wall 14. When telescoping the inner shell 18 into the released position the inner shell 18 acts as a plunger which delivers the flowable substance contained in the reservoir 38 through the orifice 32 into the applicator element 30 so that by means thereof the flowable substance is applied to the skin site requiring treatment.

In producing the released position the end portion of the sponge 30 is forced by the pin 34 to protrude from the inner shell 18 to facilitate applying the flowable substance.

Figure 3:
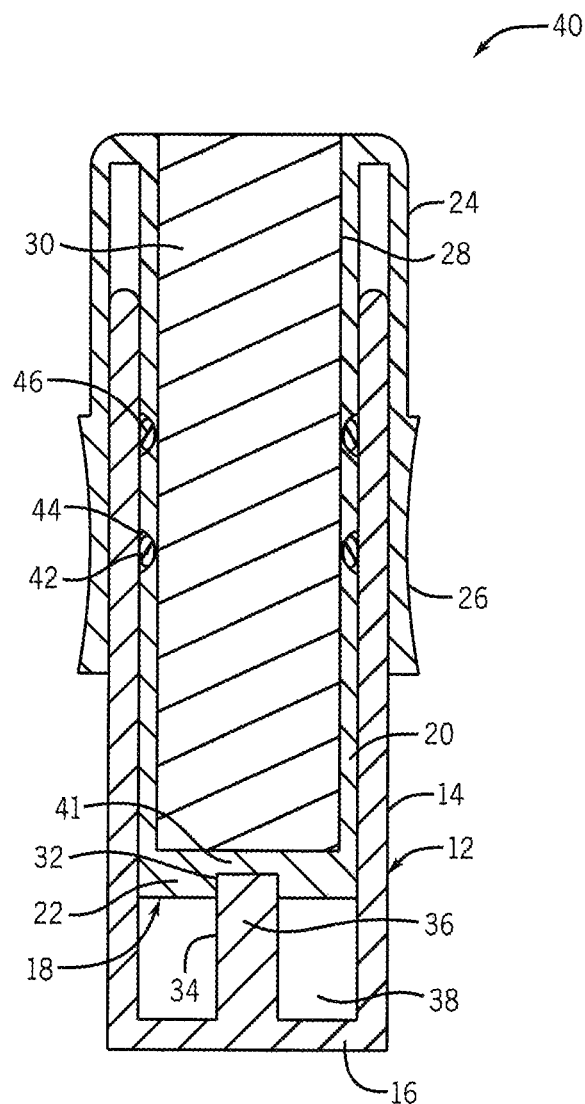
FIG. 3 is a longitudinal section through a second embodiment of the applicator device.

Referring now to FIG. 3 there is illustrated an alternative embodiment of an applicator device for applying a flowable substance. The applicator device 40 corresponds substantially to that as shown in FIGS. 1 and 2 with the difference that it is now not the pin 34 serving as the means for closing the orifice 32 but that the orifice 32 is formed by means of a thin portion 41 of the inner bottom 22 of the inner shell 18 configured as a frangible knockout. When telescoping together the applicator device 40, i.e. in producing the released position the pencil-shaped, cylindrical pin 34 configured without a portion of enlarged diameter pierces the frangible knockout or portion of reduced wall thickness 41, so that the orifice 32 is partly released and the liquid held in the reservoir 38 can flow into the sponge 30 by being dispelled.

The outer circumferential wall 14 of the outer shell 12 features furthermore on its inner surface a sealing lip 42 configured as an annular collar which cooperates with two annular grooves 44 and 46 at the outer surface of the circumferential wall 20 of the inner shell 18. The annular groove 44 defines the closed position of the applicator device 40 and an annular groove 46 defines the released position of the applicator device 40. The annular grooves 44 and 46 have in addition to their sealing function a detent function for the sealing lip 42 so that the user of the device in accordance with the invention receives a tactile impression of having attained the released position.

LIST OF REFERENCE NUMERALS 10 applicator device
12 outer shell
14 circumferential wall
16 bottom
18 inner shell
20 circumferential wall
22 bottom
24 shroud
26 annular collar
28 interior
30 applicator element
32 orifice
34 pin
36 end portion
38 reservoir
40 applicator device
41 portion of reduced wall thickness
42 sealing lip
44 annular groove
46 annular groove

The invention claimed is:

1. An applicator device for applying a flowable substance comprising:
    an outer shell which has an outer circumferential wall and an outer bottom;
    an inner shell which has an inner circumferential wall and an inner bottom and which, guided gas-tight in the outer shell, is telescopable between a closed position and a released position, the inner bottom of the inner shell including at least one orifice, which in the closed position of the inner shell is closed off by a closure means and in the released position of the inner shell allows the flowable substance to pass through at least partially, whereby in telescoping the inner shell from the closed position into the released position an inner space of the inner shell is charged by displacement of the flowable substance received in a reservoir between the outer shell and the inner shell; and
    a pin forming at least part of the closure means, said pin being at the bottom of the outer shell is axially oriented relative to the outer shell and which in the closed position of the inner shell seals tide orifice in the inner bottom of the inner shell.

2. flee applicator device as set forth in claim 1, including an applicator element engaging the inner shell at least partly.

3. The applicator device as set forth in claim 2, in which the applicator element includes a sponge.

4. The applicator device as set forth in claim 2, in which the applicator element is connected to the pin configured at the outer bottom of the outer shell.

5. The applicator device as set forth in claim 1, in which the pin comprises at its end proximal to the outer bottom of the outer shell a widened portion, the cross-sectional area of which substantially corresponds to the cross-sectional area of the orifice.

6. The applicator device as set forth in claim 1, in which the inner shell is provided with a finger-grip.

7. The applicator device as set forth in claim 6, in which the finger-grip is configured as a shroud shrouding at least partly the outer surface of the circumferential wall of the outer shell at least partly in the released position.

8. The applicator device as set forth in claim 1, in which a sealing means is disposed between the inner shell and the outer shell.

9. The applicator device as set forth in claim 8, in which the sealing means includes a sealing lip cooperating with at least one annular groove.

10. The applicator device as set forth in claim 1, in which a detent defines at least one of the closed position and the released position.

11. An applicator device for applying a flowable substance comprising;
    an outer shell which has an outer circumferential wall and an outer bottom;
    an inner shell which has an inner circumferential wall and an inner bottom and which, guided gas-tight in the outer shell, is telescopable between a closed position and a released position, the inner bottom of the inner shell including at least one orifice, which in the closed position of the inner shell is closed off by a closure means and in the released position of the inner shell allows the flowable substance to pass through at least partially, whereby in telescoping the inner shell from the closed position into the released position, an inner space of the inner shell is charged by displacement of the flowable substance received in a reservoir between the outer shell and the inner shell; and
    a pin at the bottom of the outer shell is axially oriented relative to the outer shell, wherein the closure means is formed by a portion of the inner bottom configured as a frangible knockout of the inner shell, the frangible knockout being pierced by the pin when the inner shell is telescoped from the closed position into the released position to release the orifice at least partly.

12. The applicator device as set forth in claim 11, in which the frangible knockout is formed by a material weakening.

13. An applicator device for applying a flowable substance comprising:
    an outer shell having an outer circumferential wall and an outer bottom;
    an inner shell sealingly received in said outer shell for telescopic movement between a closed position and a released position, said inner shell having an inner circumferential wall and an inner bottom defining an inner space;
    a reservoir defined between said outer shell and said inner shell for receiving the flowable substance;
    at least one orifice formed in the inner bottom of the inner shell, wherein in said released position of said inner shell said at least one orifice is in fluid communication with said reservoir allowing at least some flowable substance disposed in said reservoir to pass through said at least one orifice, whereby in telescoping the inner shell from the closed position into the released position said inner space of the inner shell is charged by displacement of the flowable substance received in the reservoir between the outer shell and the inner shell; and
    a closure means closing off said at, least one orifice in said closed position, wherein at least one pin forming at least part of said closure means extends from said outer shell, said at least one pin being axially oriented relative to the outer shell and which in the closed position of the inner shell seals the at least one orifice in the inner bottom of the inner shell.

* * * * *

UNITED STATES PATENT AND TRADEMARK OFFICE
CERTIFICATE OF CORRECTION

PATENT NO. : 9,004,796 B2  
APPLICATION NO. : 12/673108  
DATED : April 14, 2015  
INVENTOR(S) : Alberto C. Sogaro Page 1 of 1

It is certified that error appears in the above-identified patent and that said Letters Patent is hereby corrected as shown below:

In the Claims

Column 5, line 45, claim 1  
"tide" should be --the--

Column 5, line 47, claim 2  
"flee" should be --The--

Signed and Sealed this
Twenty-ninth Day of September, 2015

Michelle K. Lee
*Director of the United States Patent and Trademark Office*